US009987501B1

United States Patent
Gattiker et al.

(10) Patent No.: US 9,987,501 B1
(45) Date of Patent: Jun. 5, 2018

(54) EXTRACTING PROTOBEAMS FOR CANCER RADIATION THERAPY

(71) Applicant: INTERNATIONAL BUSINESS MACHINES CORPORATION, Armonk, NY (US)

(72) Inventors: Anne E. Gattiker, Austin, TX (US); Damir A. Jamsek, Austin, TX (US); Sani R. Nassif, Austin, TX (US); Tom Osiecki, Austin, TX (US); Chin Ngai Sze, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/370,953

(22) Filed: Dec. 6, 2016

(51) Int. Cl.
*G06K 9/00* (2006.01)
*A61N 5/10* (2006.01)

(52) U.S. Cl.
CPC .......... *A61N 5/103* (2013.01); *A61N 5/1077* (2013.01); *A61N 2005/1087* (2013.01)

(58) Field of Classification Search
None
See application file for complete search history.

(56) References Cited

U.S. PATENT DOCUMENTS 8,986,186 B2   3/2015   Zhang et al.

OTHER PUBLICATIONS

Bednarz, Ph.D., Bryan, "Monte Carlo Methods in Proton Therapy," Oct. 2005, Powerpoint Presentation (39 pages).
Paganetti, Harald et al., "Proton Beam Radiotherapy—The State of the Art," New Technologies in Radiation Oncology (Medical Radiology Series), Oct. 2005, pp. 1-36, Massachusetts General Hospital, Boston, MA, USA.
Li, Yupeng et al., "An efficient dose calculation strategy for intensity modulated proton therapy," Physics in Medicine and Biology, Jan. 2011, pp. N71-N84, Phys. Med. Biol. 56 (2011), 2011 Institute of Physics and Engineering in Medicine.

(Continued)

*Primary Examiner* — Atiba O Fitzpatrick
(74) *Attorney, Agent, or Firm* — Tutunjian & Bitetto, P.C.; William J. Stock

(57) ABSTRACT

A method and system are provided. The method includes condensing, by a processor, an original voxel-beamlet matrix stored in a memory device into a reduced dataset for proton beam simulation and therapy. The original voxel-beamlet matrix has a row for each of a plurality of voxels in a three-dimensional patient volume and a column for each of a plurality of radiation beamlets. The condensing step includes determining protobeams to be extracted from the original voxel-beamlet matrix. The protobeams are columns (i) selected from the original voxel-beamlet matrix based on comparisons performed between the columns in the original voxel-beamlet matrix or (ii) created by combining at least some of the columns in the original voxel-beamlet matrix, in a matrix condensing process. The condensing step further includes extracting the protobeams from the original voxel-beamlet matrix. The condensing step also includes storing the protobeams as the reduced dataset in the memory device.

20 Claims, 6 Drawing Sheets

(56) References Cited

OTHER PUBLICATIONS

Ericsson, Malin, "Intensity Modulated Proton Therapy (IMPT)—A comparative treatment planning study," Master of Science Thesis, Jan. 2007, pp. 1-76, Department of Radiation Physics, Lund University Hospital, Medical Radiation Physics Clinical Sciences, Lund, Lund University.
Breedveld, Sebastiaan et al., "A novel approach to multi-criteria inverse planning for IMRT," Physics in Medicine and Biology, Oct. 2007, pp. 6339-6353, Phys. Med. Biol. 52 (2007), 2007 IOP Publishing Ltd.
Gonzalo, Cabal et al., "Target Definition and Treatment Planning in Particle Therapy using Monte Carlo Error Propagation Analysis," Powerpoint Presentation, 1st New Mexico Workshop on Monte Carlo for Particle Therapy Treatment Planning Albuquerque, New Mexico May 16-18, 2011 (45 pages).
Chen, Wei et al., "A fast optimization algorithm for multicriteria intensity modulated proton therapy planning," American Association of Physicists in Medicine, Aug. 2010, pp. 4938-4945, Med. Phys. 37 (9).
Chvetsov, Alexei V. et al., "Regularization of inverse planning for intensity-modulated radiotherapy," American Association of Physicists in Medicine, Jan. 2005, pp. 501-514, Med. Phys. 32 (2).
Gui, Yi et al., "Constrained Grouped Sparsity," Conference Paper, Dec. 2012, pp. 1-27, Proceedings of the 25th Australasian joint conference on Advances in Artifcial Intelligence.
Fredricksson, Albin, "Automated Improvement of Radiation Therapy Treatment Plans by Optimization Under Reference Dose Constraints," Physics in Medicine and Biology 57, Nov. 2012, pp. 7799-7811.
Friedman, Jerome et al., "A note on the group lasso and a sparse group lasso," arXiv preprint arXiv, Jan. 2010, pp. 1-8, 1001.0736.
Holdsworth, Clay et al., "The use of a multiobjective evolutionary algorithm to increase flexibility in the search for better IMRT plans," American Association of Physicists in Medicine, Apr. 2012, pp. 2261-2274, Med. Phys. 39 (4).
Petit, Steven et al., "Increasing maximum tumor dose to manage range uncertainties in IMPT treatment planning," Physics in Medicine and Biology, Sep. 2013, pp. 7329-7341, Phys. Med. Biol. 58 (2013), 2013 Institute of Physics and Engineering in Medicine.
Lim, Gino J. et al., "A two-phase method for selecting IMRT treatment beam angles: Branch-and-Prune and local neighborhood search," European Journal of Operational Research, Feb. 2012, pp. 609-618, 217 (3).
Lim, Gino J. et al., "Iterative Solution Methods for Beam Angle and Fluence Map Optimization in Intensity Modulated Radiation Therapy Planning," OR Spectrum, Apr. 2008, pp. 289-309, 30 (2).
Unkelbach, Jan et al., "The dependence of optimal fractionation schemes on the spatial dose distribution," Physics in medicine and biology, Dec. 2012, pp. 1-14, 58(1) 159.
Chen, Wei et al., "Including Robustness in Multi-criteria Optimization for Intensity Modulated Proton Therapy," Department of Radiation Oncology, Massachusetts General Hospital and Harvard Medical School, Dec. 2011, pp. 1-17, arXiv 1112.5362 v1.
Craft, David L. et al., "Approximating convex Pareto surfaces in multiobjective radiotherapy planning," American Association of Physicists in Medicine, Aug. 2006, pp. 3399-3407, Med. Phys. 33 (9).
Fredriksson, Albin et al., "Minimax optimization for handling range and setup uncertainties in proton therapy," American Association of Physicists in Medicine, Mar. 2011, pp. 1672-1684, Med. Phys. 38 (3).
Paganetti, Harald, "Range uncertainties in proton therapy and the role of Monte Carlo simulations," Phys Med Biol. Jun. 2012, pp. 1-27, 57 (11).
Cao, Wenhua et al., "Beam angle selection in Intensity Modulated Proton Therapy treatment planning for prostate cancer," Proceedings of the 2011 Industrial Engineering Research Conference, Jan. 2011, pp. 2-8.
Siebers, Ph.D, Jeffrey V. et al., "Monte Carlo Applications in IMRT Planning and Quality Assurance," Proceedings of the 2006 AAPM Summer School, edited by I. Chetty (Medical Physics Publishing Corp, Madison, WI, 2006), Jun. 2006, pp. 1-33.
Iordache, Marian-Daniel et al., "Hyperpectral Unmixing with Sparse Group Lasso," Geoscience and Remote Sensing Symposium (IGARSS), Oct. 2011, pp. 3586-3589, 2011 IEEE International.
Kim, Taeho et al., "Inverse planning for IMRT with nonuniform beam profiles using total-variation regularization (TVR)," American Association of Physicists in Medicine, Dec. 2010, pp. 57-66, Med. Phys. 38 (1).
Zhu, Lei et al., "Using total-variation regularization for intensity modulated radiation therapy inverse planning with field-specific numbers of segments," Phys. Med. Biol., Nov. 2008, pp. 6653-6672, 53 (2008).
Tibshirani, Robert, "Regression shrinkage and selection via the lasso: a retrospective," Journal of the Royal Statistical Society, Sep. 2011, pp. 273-282, B (2011) 73, Part 3.
Simon, Noah et al., "Standardization and the Group Lasso Penalty," Statistica Sinica, Jul. 2012, pp. 1-21.
Unkelbach, Jan et al., "Reducing the sensitivity of IMPT treatment plans to setup errors and range uncertainties via probabilistic treatment planning," American Association of Physicists in Medicine, Dec. 2008, pp. 149-164, Med. Phys. 36 (1).
Xia, Ph. D, Ping, "Inverse Planning Techniques for IMRT," Powerpoint Presentation, Jul. 2004, (22 pages).
Liu, Wei et al., "Effectiveness of robust optimization in intensity-modulated proton therapy planning for head and neck cancers," American Association of Physicists in Medicine, Apr. 2013, pp. 051711-1-051711-9, Med. Phys. 40 (5).
Cao, Wenhua et al., "Proton energy optimization and reduction for intensity-modulated proton therapy," Phys Med Biol., Nov. 2014, pp. 6341-6354, 59 (21).
Cao, Wenhua et al., "Incorporating deliverable monitor unit constraints into spot intensity optimization in intensity modulated proton therapy treatment planning," Phys Med Biol., Aug. 2013, pp. 5113-5125, 58 (15).
Liu, Wei et al., "Robust optimization of intensity modulated proton therapy," American Association of Physicists in Medicine, Feb. 2012, pp. 1079-1092, Med. Phys. 39 (2).
Yuan, Ming et al., "Model selection and estimation in regression with grouped variables," J. R. Statist., Nov. 2006, pp. 49-67, Soc. B (2006) 68, Part 1.

EXTRACTING PROTOBEAMS FOR CANCER RADIATION THERAPY

BACKGROUND

Technical Field

The present invention relates generally to radiation therapy and, in particular, to extracting protobeams for cancer radiation therapy.

Description of the Related Art

Proton (or other heavier ions such as carbon) Beam Radiation Therapy Treatment for cancer aims to shoot protons from a source into the body in such a way that the protons deposit a large amount of energy into the tumor, while minimizing the amount of energy deposited into healthy tissue. The tumor is referred to as the target volume, using terms such as clinical target volume (CTV), scanning target volume (STV), and planning target volume (PTV), while parts of the healthy tissue to be avoided are termed Organs at Risk, or OARs. Treatment planning involves choosing the energies of the proton beams that are shot, as well as the angles from which they are shot and calculating the optimal duration at a given current for each energy-angle pair. Assuming pencil beam therapy, the time for each beamlet in a scan matrix of beamlets is determined. Planning is usually done using the outputs of a particle simulator that indicates where in the patient's body candidate protons of different energies and shot from different angles drop their energy. A solution to the treatment planning problem determines, using those outputs and a knowledge of the target energies desired in each body region, how much energy and from which angles to shoot protons as well as for how long at a given current. Typically that problem is solved using Linear or Quadratic Programming optimization approaches, but the large size of the relevant matrices in the mathematical formulation of the problem can make solution times unacceptably slow. In addition to the size of the matrices, correlation within them can lead to slow solutions of unacceptable or unstable quality.

SUMMARY

According to an aspect of the present principles, a method is provided. The method includes condensing, by a processor, an original voxel-beamlet matrix stored in a memory device into a reduced dataset for proton beam simulation and therapy. The original voxel-beamlet matrix has a row for each of a plurality of voxels in a three-dimensional patient volume and a column for each of a plurality of radiation beamlets. The condensing step includes determining protobeams to be extracted from the original voxel-beamlet matrix. The protobeams are columns (i) selected from the original voxel-beamlet matrix based on comparisons performed between the columns in the original voxel-beamlet matrix or (ii) created by combining at least some of the columns in the original voxel-beamlet matrix, in a matrix condensing process. The condensing step further includes extracting, by a hardware processor, the protobeams from the original voxel-beamlet matrix. The condensing step also includes storing the protobeams as the reduced dataset in the memory device.

According to another aspect of the present principles, a computer program product for extracting protobeams is provided. The computer program product includes a computer readable storage medium having program instructions embodied therewith, the program instructions executable by a computer to cause the computer to perform a method. The method includes condensing, by a processor, an original voxel-beamlet matrix stored in a memory device into a reduced dataset for proton beam simulation and therapy. The original voxel-beamlet matrix has a row for each of a plurality of voxels in a three-dimensional patient volume and a column for each of a plurality of radiation beamlets. The condensing step includes determining protobeams to be extracted from the original voxel-beamlet matrix. The protobeams are columns (i) selected from the original voxel-beamlet matrix based on comparisons performed between the columns in the original voxel-beamlet matrix or (ii) created by combining at least some of the columns in the original voxel-beamlet matrix, in a matrix condensing process. The condensing step further includes extracting, by a hardware processor, the protobeams from the original voxel-beamlet matrix. The condensing step also includes storing the protobeams as the reduced dataset in the memory device.

According to yet another aspect of the present principles, a system is provided. The system includes a memory device configured to store an original voxel-beamlet matrix having a row for each of a plurality of voxels in a three-dimensional patient volume and a column for each of a plurality of radiation beamlets. The system further includes a hardware processor configured to condense the original voxel-beamlet matrix into a reduced dataset for proton beam simulation and therapy by determining protobeams to be extracted from the original voxel-beamlet matrix, and extracting the protobeams from the original voxel-beamlet matrix. The protobeams are columns (i) selected from the original voxel-beamlet matrix based on comparisons performed between the columns in the original voxel-beamlet matrix or (ii) created by combining at least some of the columns in the original voxel-beamlet matrix, in a matrix condensing process. The protobeams are stored as the reduced dataset in the memory device.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
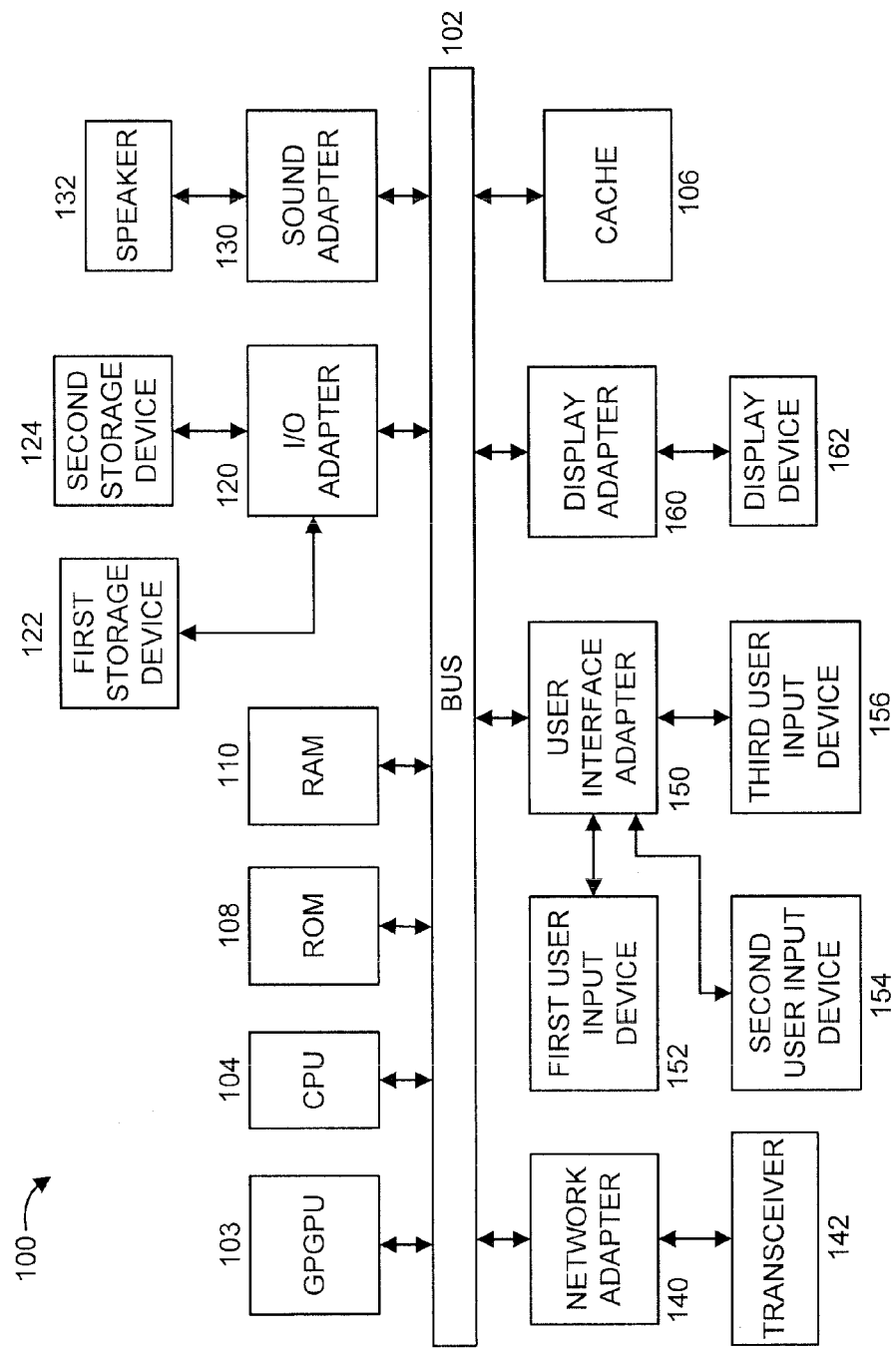
FIG. 1 shows an exemplary processing system 100 to which the present principles may be applied, in accordance with an embodiment of the present principles.

The present principles are directed to extracting protobeams for cancer radiation therapy. The radiation treatment planning problem takes as input a v×b voxel-beamlet matrix, vbmat, along with clinical criteria (desired dose) and produces a b element vector that gives the duration at a given current for each of b beamlets to be used during treatment. The treatment planning problem is typically solved by Quadratic Programming (QP) or Linear Programming (LP) optimization approaches. As used herein, the term "protobeam" refers to a column of a reduced matrix, vpbmat, which can be used in place of vbmat in finding solutions to the treatment planning problem. Each protobeam is a v-element vector that describes an amount of energy deposited in each of v voxels. The protobeams are concatenated columnwise to create the v×pb reduced matrix, vpbmat, where typically pb<b. Embodiments herein describe ways protobeams can be extracted. In the context of protobeams, the term "extracting" is used herein to refer to selecting existing columns from vbmat or to calculating new v-element vectors that are weighted combinations of existing columns of vbmat.

In an embodiment, the present principles extract "protobeams" that provide a reduced representation of the treatment planning problem. This reduced representation enables faster and higher quality solutions to the treatment planning problem.

Typically, the outputs of a particle simulation are captured in a matrix referred to herein as vbmat. A vbmat has a row for each voxel in a 3-D patient volume and a column for each beamlet. Cells (entries) of the vbmat give the energy deposited in the row's voxel when the column's beamlet is applied for a known duration and current. A beamlet is a stream of protons of a given energy shot from a given angle at a given location in the scan matrix, where the scan matrix is the typically two-dimensional set of locations from which beamlets are shot. We use the term "physical delivery system settings" to refer to properties of the physical delivery system that are set to create a given beamlet, such as angle, energy and scan matrix location. These settings differ beamlet to beamlet. Each voxel is identified as belonging to a given body region, e.g., the target volume (aka STV) or an Organ At Risk (aka OAR). Targets are set based on the amount of energy desired to be deposited in a given body region.

The size of the relevant matrices makes solutions difficult. Moreover, the vbmat typically has significant and complex correlation within it which, in turn, can make solutions, such as Quadratic Programming (QP), Linear Programming (LP) and regression, difficult.

The present principles extract protobeams which well-represent the original problem with reduced matrices. The number of protobeams extracted is variable and can be determined based on metrics measuring the representation quality and/or computation-ease versus the number of beams and also the needed representation quality and/or computation-ease. The needed quality and/or computation ease can vary based on, for example, but not limited to, the stage of the overall treatment planning process. For example, early in a treatment planning process, rough planning may take place for which needed representation quality is relative low. The rough planning could be used to explore, for example, different solution methods such as choice of optimization approach. Early in a treatment planning process, computation ease may be a priority so that a large number of options can be explored quickly. The number of protobeams extracted can also be determined based on a trade-off between representation quality and computation ease. In an embodiment, the protobeams are weighted combinations of columns from the original vbmat. In other embodiments they are columns selected from the original vbmat.

An attribute of protobeams in accordance with the present principles is that they are physically realistic, that is, the protobeams represent energy deposited by a real, feasible combination of beamlets. Moreover, desired qualities of the extraction methods are size decrease and correlation reduction. Once extracted, the protobeams can be used as a smaller, more efficient proxy to vbmat in solutions to the treatment planning problem.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
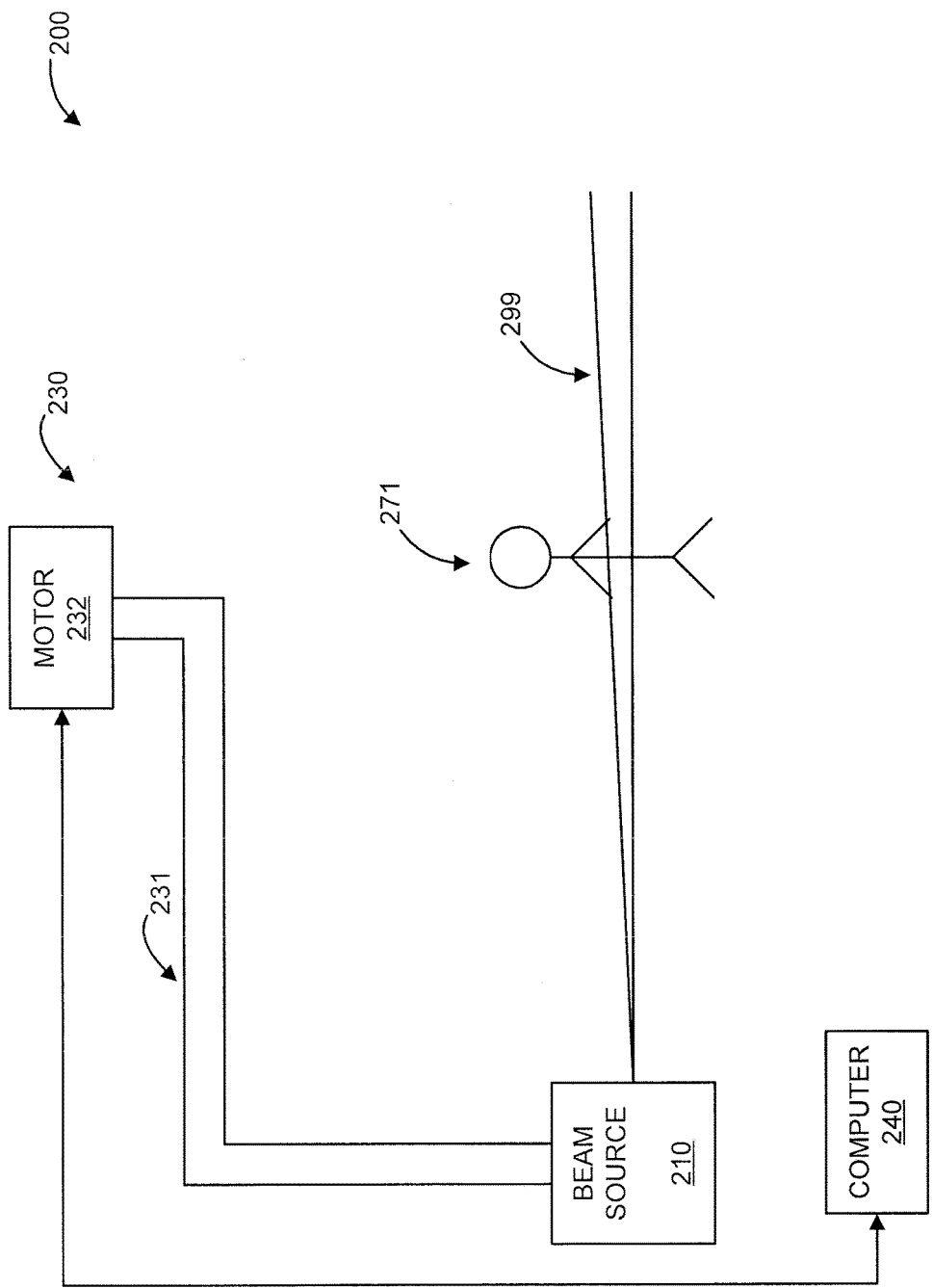
FIG. 2 shows an exemplary radiation therapy system 200 to which the present principles can be applied, in accordance with an embodiment of the present principles.

Moreover, it is to be appreciated that system 200 described below with respect to FIG. 2 is a system for implementing respective embodiments of the present principles. Part or all of processing system 100 may be implemented in one or more of the elements of system 200.

Further, it is to be appreciated that processing system 100 may perform at least part of the method described herein including, for example, at least part of method 300 of FIGS.

3-4. Similarly, part or all of system 200 may be used to perform at least part of method 300 of FIGS. 3-4.

FIG. 2 shows an exemplary radiation therapy system 200 to which the present principles can be applied, in accordance with an embodiment of the present principles.

The radiation therapy system 200 includes a beam source 210, a positional device 230, and a computer 240.

The beam source 210 provides a radiation source for emitting radiation 299 to a target structure. In an embodiment, the beam source 210 can include a particle accelerator. In an embodiment, the beam source generates beamlets. Assuming proton pencil beam therapy, a beamlet is a stream of protons of a given energy shot from a given angle at a given location in a scan matrix.

The positional device 230 is attached to and positions the beam source 210 relative to an object of interest (person) 271 to emit radiation to one or more target structures (e.g., cancer tumors) in the object of interest. Often, the positional device 230 includes a structural member 231 to secure the beam source 210 for positioning, and a motor 232 to position the structural member 231 with respect to the one or more target structures.

The computer 240 controls the elements of system 200. For example, the computer 240 activates the beam source 210, and controls the movement of the positional device 230. Wiring for such control can be within the structural member 231 or in some other arrangement. The computer 240 includes a processor 240A and a memory 240B. The processor 240A initiates the controlling of the other elements including, for example, the emission of radiation by the beam source 210. The memory 240B stores software for performing a radiation therapy process. The memory 240B can also store data generated during a radiation therapy process.

It is to be appreciated that the present principles are not dependent upon any particular type of radiation therapy system and, thus, can be used with any type of radiation therapy system, while maintaining the spirit of the present principles. Thus, it is to be further appreciated that system 200 is generally described and can include other elements and other capabilities, as readily recognized by one of ordinary skill in the art. Moreover, while system 200 is described in one embodiment as involving protons, systems employing other types of radioactive elements can also be used in accordance with the teachings of the present principles, while maintaining the spirit of the present principles. These and other variations of system 200, as well as other radiation therapy systems to which the present principles can be applied, are readily determined by one of ordinary skill given the teachings of the present principles provided herein, while maintaining the spirit of the present principles.

Figure 3:
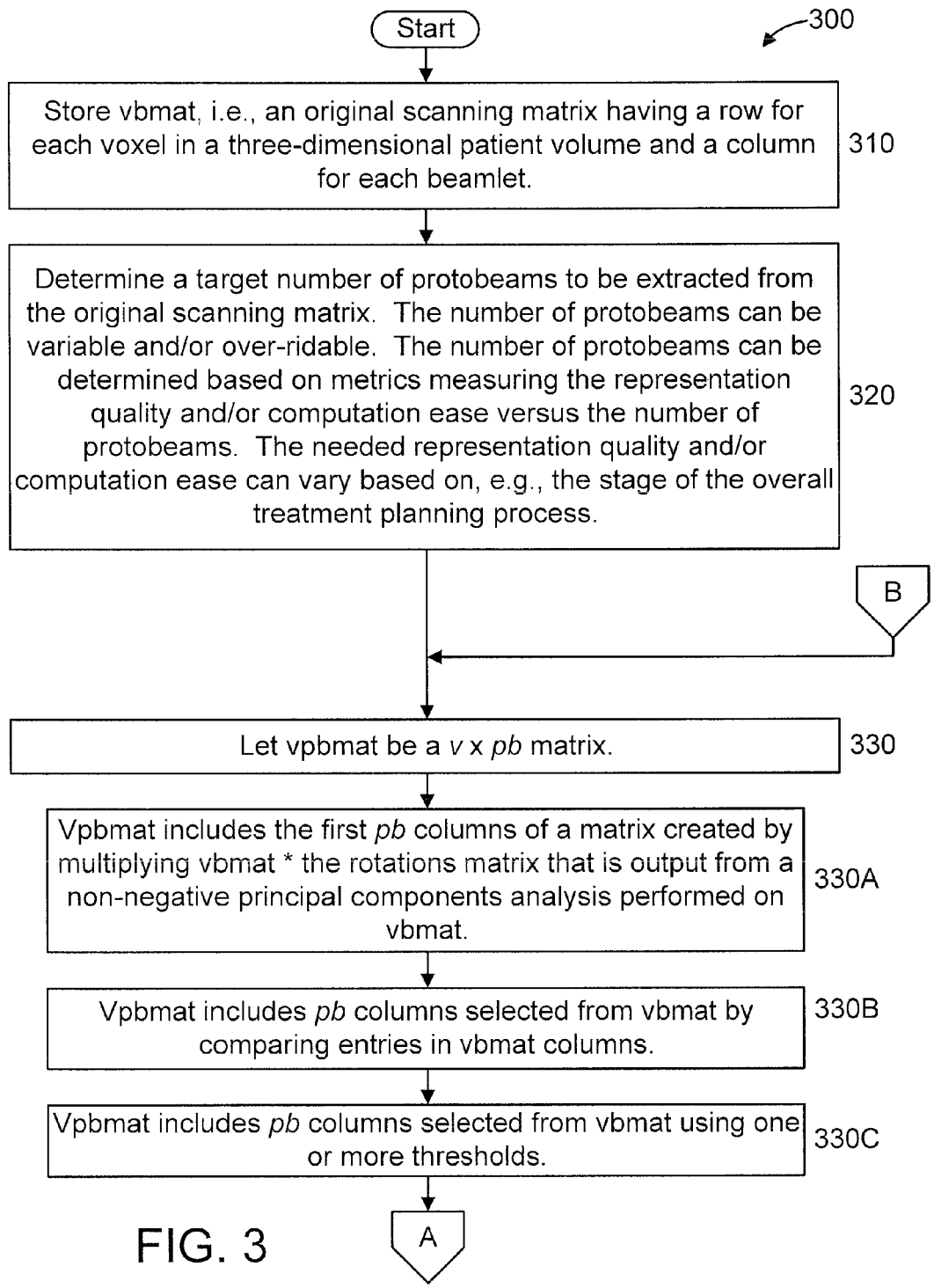
FIGS. 3-4 show an exemplary method 300 for extracting protobeams for cancer radiation therapy, in accordance with an embodiment of the present principles.
Figure 4:
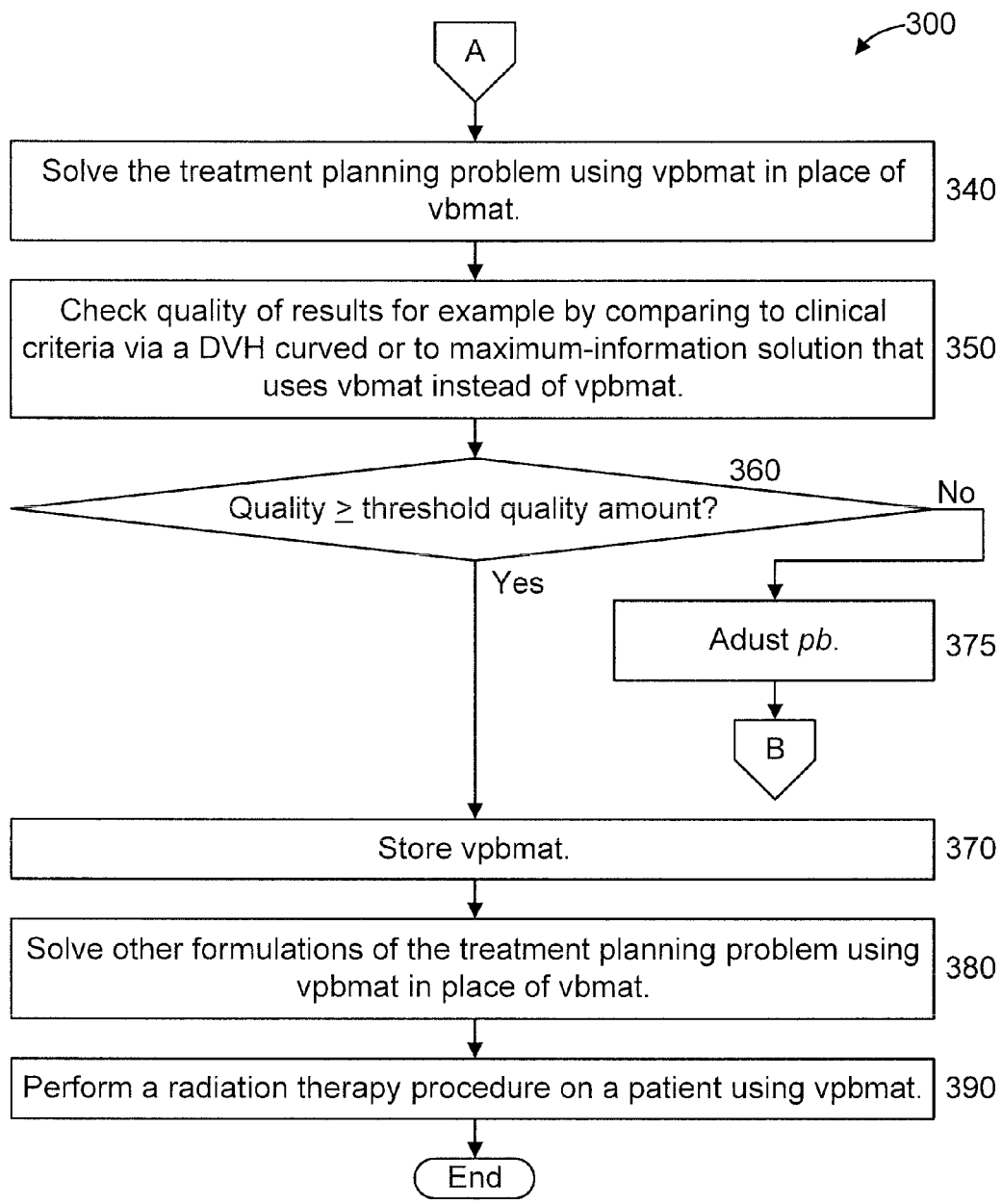

FIGS. 3-4 show an exemplary method 300 for extracting protobeams for cancer radiation therapy, in accordance with an embodiment of the present principles.

At step 310, store vbmat, i.e., an original voxel-beamlet matrix having a row for each voxel in a three-dimensional patient volume and a column for each beamlet.

At step 320, determine number of protobeams, pb, to be extracted from vbmat. In an embodiment, the number of protobeams that are extracted is variable and/or over-ridable. In an embodiment, the number of protobeams that are extracted can be determined based on metrics measuring the representation quality and/or computation ease versus the number of protobeams and also on metrics measuring the needed representation quality and/or computation ease versus the number of protobeams. The needed representation quality and/or computation ease can vary based on, for example, but not limited to, the stage of the overall treatment planning process. Experience with data from prior patient cases, for example, can be used to estimate relationships of representation quality and/or computation ease versus number of protobeams. The representation quality for a given number of protobeams can be measured, for example, against a maximum information representation that uses the entire original vbmat. The comparison can be done, for example, by running a treatment planning with both representations and evaluating the similarity of the results where results can be captured for example via a Dose-Volume-Histogram (DVH) curve or using any data representation. An approximation or simplified metric that avoids running a treatment planning can alternatively be used, e.g., the fraction of the number of target voxels having a summed dose greater than a threshold in the original matrix can be compared with the fraction of the number of target voxels having a summed dose greater than a threshold in the reduced matrix comprising only protobeams. As another alternative, measures of correlation within vbmat can be used to measure representation quality, where typically very high correlation, e.g., colinearity or near-colinearity, among columns would diminish quality. Computation ease can be measured, for example, by computation time or memory requirements of a computation that operates on the reduced matrix. A corresponding metric can be as simple as memory size required to hold the matrix or involve running a computation using the reduced matrix, where the computation could be running a treatment planning, or a simpler computation such as inverting the reduced matrix or a function of it. Computation ease can be a function of and potentially measured by matrix size and/or amount of correlation among the matrix's columns. Correlation among columns can affect computation ease. These and other considerations for determining the target number of protobeams to be extracted are readily determined by one of ordinary skill in the art, given the teachings of the present principles provided herein, while maintaining the spirit of the present principles.

At step 330, let vpbmat be a v×pb matrix (note that this is "vpbmat", and not the "vbmat" stored at step 310).

In an embodiment, step 330 can include any of steps 330A, 330B, and 330C, also interchangeably referred to as "Option 1", "Option 2", and "Option 3".

At step 330A ("Option 1"), vpbmat includes the first pb columns of a matrix created by multiplying vbmat*the rotations matrix that is output from a non-negative principal components analysis performed on vbmat. That is, a rotated version of vbmat (call it N) is calculated as vbmat multiplied by a rotation matrix (call it P), where the rotation matrix is determined by performing a non-negative principal components analysis on vbmat. The columns of N are the principal components. Because non-negative constraints may result in non-pairwise orthogonality of the columns of P it may be considered a "pseudo-rotation matrix." Although non-negative constraints may result in non-pairwise orthogonality of the columns of P, each column can be chosen such that the additional variance not explained by the previous components is maximized. The non-negative principal components analysis can be carried out, for example, using the R function nsprcomp. For simplicity of explanation, it is assumed no centering or scaling is performed. Each column of the b×b rotation matrix P determined in the non-negative components analysis procedure is a principal axis and its elements are the loadings. Each principal axis specifies a linear combinations of the b beamlets and the loadings give the weight of each beamlet in the linear combination. In non-negative principal components, the loadings are non-negative. N=vbmat×P. Since each subsequent column of P is chosen in order based on maximizing the additional variance not explained by previous components, choosing pb<b protobeams as the first pb columns in N and concatenating them columnwise in order to create vpbmat allows vpbmat to include much of the information from vbmat in a matrix that is smaller. The smaller matrix is easier to work with when exploring solutions to the treatment planning problem. Moreover, the correlation among components of vpbmat may be reduced as compared with vbmat, which also helps treatment planning solution methods create better solutions At step 330B ("Option 2"), vpbmat includes pb columns selected from vbmat by comparing entries in vbmat columns. An example algorithm for choosing the set of protobeams to concatenate columnwise to create vpbmat follows. The set of protobeams is the set of columns of vbmat corresponding to all beamlets not eliminated by the following. Create a comparison set containing the b beamlets in vbmat. For each of the b beamlets $b_j$ in vbmat, compare $b_j$ to each of the other beamlets $b_i$ in the comparison set. The column corresponding to $b_j$ can be eliminated from the set of protobeams chosen from vbmat when the following pseudocode returns "true" for the comparison of $b_j$ to any of the $b_i$. If $b_j$ is eliminated according to the pseudocode, remove it from the comparison set before moving to the next beamlet.
Result=true
For each voxel cluster $VC_k$ {
    Condition 1: If $VC_k$ is in target volume (i.e., it requires a high dose), if (sum of dose of $b_j$ at voxels belonging to $VC_k$)>(sum of dose of $b_i$ at voxels belonging to $VC_k$) then set result=false
    Condition 2: If $VC_k$ is in organ at risk (i.e., it requires a low dose), if (sum of dose of $b_j$ at voxels belonging to $VC_k$)<(sum of dose of $b_i$ at voxels belonging to $VC_k$) then set result=false
}
Return result The set of all vbmat columns corresponding to beamlets not eliminated by the above algorithm are the protobeams. Please note that in an embodiment a voxel cluster can be a single voxel or a group of voxels as large as a whole structure (e.g., STV or given OAR). Using a larger voxel cluster can lead to skipping more beamlets, i.e., choosing fewer protobeams. A voxel cluster is always covered by a structure. In other words, a voxel cluster cannot include voxels from more than one structure.

At step 330C ("Option 3"), vpbmat includes a column selected from vbmat based on one or more thresholds. For example, perform step 330B and, as a variation of step 330B, also include a threshold for one or both conditions. That is, rather than requiring complete dominance of one beamlet over another, use a threshold, e.g., in each of Condition 1 and Condition 2, and multiply the left hand side of the equality symbol by a threshold value, e.g., 0.9 for Condition 1 and 1.1 for Condition 2. The threshold can be varied to extract different numbers of protobeams, depending upon the implementation.

Note that beamlet selection in step 330C and step 330D ("Option 2" and "Option 3") require only limited information and simple calculations to select beamlets. They can be carried out using only the vbmat entries and labels for each vbmat row, i.e., for each voxel, giving the structure membership, e.g., target or OAR. The example algorithm's steps operate on voxel clusters, but if simple voxel clustering is done, e.g., each voxel is a cluster, or each structure is a cluster, no further information is needed. If more complicated voxel clustering is done, the cluster membership for each cluster is needed. Cluster membership can be based on, for example, mathematical correlation within vbmat, which requires only knowledge of vbmat and voxel-structure labels. Alternatively it can be based on criteria that require additional knowledge, such as physical proximity of voxels to one another. No information on the physical delivery system attributes of the beamlets corresponding to the vbmat columns is needed, e.g., angles of the beamlets relative to one another or to the patient or knowledge of the voxel location relative to the patient surface or radiation source is necessary. Moreover, no clinical criteria or resulting objective function is needed and running treatment planning (e.g., done via optimization) is not required.

In Option 3, clinical criteria can optionally be used to guide choice of thresholds, but an objective function and running treatment planning are not required.

At step 340, solve the treatment planning problem using vpbmat in place of vbmat. The result is a vector that gives a multiplication factor for each column of vpbmat. For Option 1, the multiplication factor is a duration at a given current for a weighted combination of beamlets. The duration for each physical beamlet can be derived by multiplying the first pb columns of the rotations matrix output from the non-negative principal component analysis times the result vector. For Options 2 and 3, the multiplication factor is a duration at a given current for a beamlet. If results quality is judged in a way (see step 350) that does not require a treatment planning solution to be calculated, step 340 can be skipped.

At step 350, check quality of results for example by comparing to clinical criteria via a DVH curve or to a maximum-information solution that uses vbmat instead of vpbmat. We use the term "quality of results" to refer to both representation quality and computation ease. Representation quality can measure, for example, whether or not the representation contains enough information to adequately gauge whether or not a solution to treatment planning that uses the representation meets clinical criteria. It can also measure how much of the information in the original matrix is contained in the reduced matrix. The representation quality of a reduced matrix comprising protobeams can be measured, for example, against a maximum information representation that uses the entire original vbmat. The comparison can be done, for example, by running a treatment planning with both representations and evaluating the similarity of the results where results can be captured for example via a Dose-Volume-Histogram (DVH) curve or using any data representation. An approximation or simplified metric that avoids running a treatment planning can alternatively be used, e.g., the fraction of the number of target voxels having a summed dose greater than a threshold in the original matrix can be compared with the fraction of the number of target voxels having a summed dose greater than a threshold in the reduced matrix comprising only protobeams. As another alternative, measures of correlation within vbmat can be used to measure representation quality, where typically very high correlation, e.g., colinearity or near-colinearity, among columns would diminish quality. For Option 1 (step 340*a*), a measure of variance explained by the principal components can be used to measure representation quality. Computation ease can be measured, for example, by computation time or memory requirements of a computation that operates on the reduced matrix. A corresponding metric can be as simple as memory size required to hold the matrix or involve running a computation using the reduced matrix, where the computation could be running a treatment planning, or a simpler computation such as inverting the reduced matrix or a function of it. Computation ease can be a function of and potentially measured by matrix size and/or amount of correlation among the matrix's columns. Correlation among columns can affect computation ease.

When step 340 is carried out, an applied dose vector that gives the radiation deposited in each voxel by the step 340 solution can be calculated. The step 340 solution is a set of weights for each column of vpbmat. The applied dose vector can be used to generate results such as a DVH curve. To calculate the applied dose vector, for Option 1, multiply vpbmat times the duration for each column of vpbmat determined in step 340 or, equivalently, multiply vbmat times the duration for each physical beamlet optionally derived in step 340. For Options 2-3, multiply vpbmat times the duration for each column of vpbmat determined in step 340 or, equivalently, create a new vector whose elements correspond to the columns of vbmat. Set elements to zero for any column of vbmat that was not chosen for vpbmat. Set elements for columns chosen for vpbmat to the time durations at a given current determined in step 340 for the corresponding columns. Multiply vbmat times the new vector.

At step 360, determine if the quality is greater than or equal to a threshold quality amount. If so, then proceed to step 370. Otherwise, proceed to step 375.

At step 370, store vpbmat.

At step 375, adjust pb and return to step 330. If all values of pb have been evaluated in previous iterations, or if the current value of pb is the only one possible and the quality is not high enough, then (unsuccessfully) terminate the process. Further, although the quality of the solution, measured for example against ability to meet clinical goals or against closeness of match between a DVH curve created using the original vbmat and a DVH curve created using vpbmat, generally increases with greater pb, because fewer protobeams can mean less correlation in vpbmat, the solution quality can also decrease with greater pb. However, it may be possible to note a trend in solution quality versus number of protobeams, in which case the process can be terminated (unsuccessfully) when a condition has been reached that is short of having evaluated all values of pb but where the trend suggests further increases or decreases of pb are unlikely to improve solution quality. Additionally, the solution can be terminated when a loop counter threshold has been reached, where the loop counter counts, for example, the number of times step 360 has been carried out.

At step 380, solve other formulations of the treatment planning problem using vpbmat in place of vbmat.

Regarding step 380, it can be helpful during treatment planning to explore different ways to set up and solve the treatment planning problem. Different set-ups include, for example, different translations from clinical criteria into optimization objective functions and constraints. Different solution methods include, for example, QP, LP and regression. Using vpbmat instead of vbmat, in other words using protobeams, makes that exploration more efficient because vpbmat is smaller and potentially contains less correlation than vbmat. The primary intention for protobeams would be this sort of exploration, rather than actually applying an approximate protobeam solution directly to a patient. However, given the right protobeams as determined from such exploration, then application to a patient can be performed.

At step 390, perform a radiation therapy procedure on a patient using vpbmat. In an embodiment, system 200 of FIG. 2 performs the radiation therapy procedure of step 390 of method 300 of FIG. 3. Of course, other types of radiation therapy/radiation emitting systems can also be used in accordance with the teachings of the present principles while maintaining the spirit of the present principles.

It is to be appreciated that solution quality, for example, measured against ability to meet clinical goals, or measured against closeness of match between a DVH curve created using the original vbmat and a DVH curve created using vpbmat, generally improves when more protobeams are used, but the solution time generally also increases. Different settings of numbers of protobeams can be chosen to trade-off computation complexity versus solution quality. Because some embodiments reduce correlation in vpbmat relative to vbmat, solution quality can also decrease with increasing numbers of protobeams, possibly after first increasing initially.

It is to be further appreciated that since the algorithm in Option 2 can find all beamlets that are dominated by other beamlets, it is possible to determine the set of beamlets eligible for elimination and use the columns corresponding to the remaining beamlets as protobeams. In that case, pb, the desired number of protobeams is not determined in advance. Instead it is given by running the algorithm. Then there would also be no pb adjusting step. In other words, steps 320 and 375 would be eliminated. If quality is insufficient at step 360, then the process would terminate unsuccessfully. Similarly in Option 3, thresholds on the conditions can be set (step 505 below) and then again it is possible to determine the set of beamlets eligible for elimination and use the columns corresponding to remaining beamlets as protobeams. In that case, pb, the desired number of protobeams, is not determined in advance. Instead it is given by running the algorithm. Then there would also be no pb adjusting step. In other words, steps 320 and 375 would be eliminated. If quality is insufficient at step 360, then the process would terminate unsuccessfully. For Option 3, another option follows. Instead of a pb adjusting step (step 375), there could be a condition-threshold adjusting step where condition-thresholds are adjusted to increase the quality of the results, e.g., thresholds on the left-hand side of Condition 1 can be increased and thresholds on the left-hand side of Condition 2 could be decreased to allow fewer beamlets to be eliminated. In other words, step 320 would be skipped and a new decision step would replace step 375. The new decision step would determine if threshold-adjustment options have been exhausted. If they have, the process terminates unsuccessfully. If they have not, the thresholds on the conditions could be adjusted, e.g., to allow fewer beamlets to be eliminated, as described above.

Please note that different thresholds can be used in Condition 1 and Condition 2, for different $VC_k$s, e.g., if $VC_k$ is in a more sensitive OAR than another voxel cluster, then the threshold on the left-hand side of Condition 2 can be lower for $VC_k$ than for the other voxel cluster. Similarly, if $VC_k$ is in a more sensitive target volume than another voxel cluster, then the threshold on the left-hand side of Condition 1 can be higher for $VC_k$ than for the other voxel cluster. Moreover, in a condition-threshold-adjusting step the condition-threshold adjustments can be different for different voxel clusters.

Figure 5:
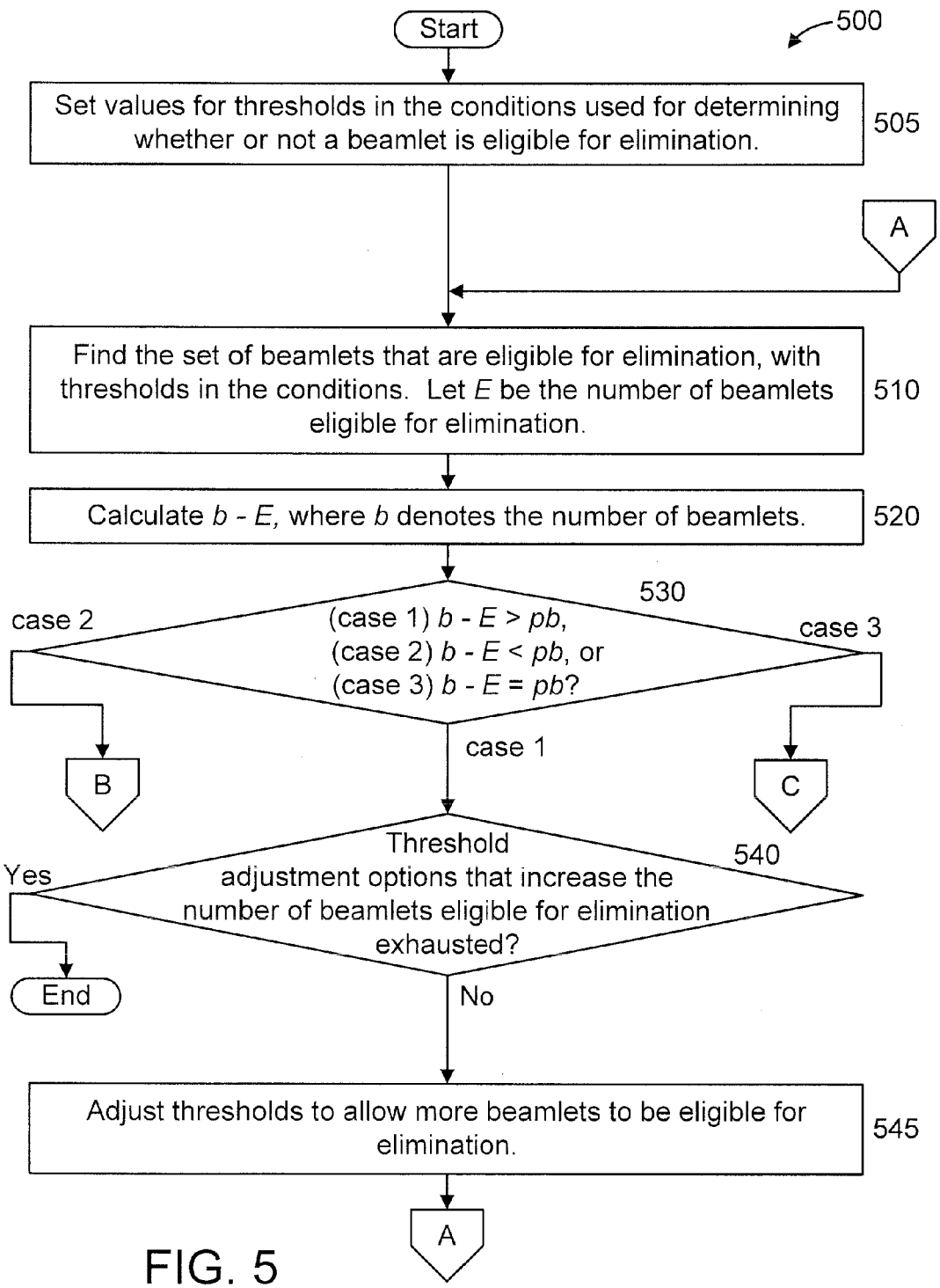
FIGS. 5-6 further show an implementation of steps 330B and 330C of FIG. 3, in accordance with an embodiment of the present principles.
Figure 6:
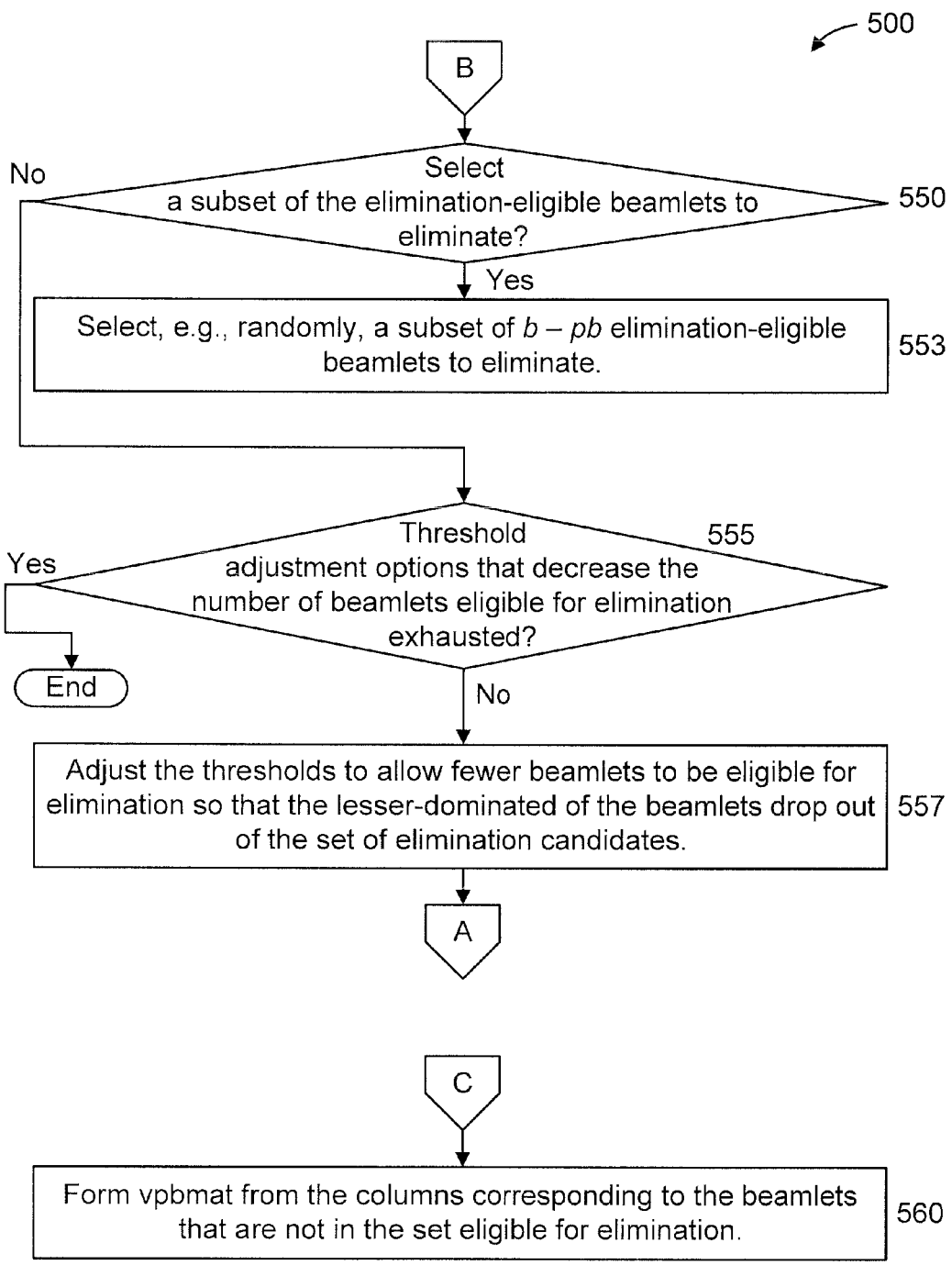

FIGS. 5-6 further show an implementation of steps 330B and 330C of FIG. 3, in accordance with an embodiment of the present principles.

At step 505, set values for thresholds in the conditions used for determining whether or not a beamlet is eligible for elimination. For 330B, the thresholds are set to one. For 330C, initial thresholds can be set based on an estimation of values that will allow a number of beamlets preferably close to but not less than b−pb to be eliminated, where b denotes the number of beamlets, if such values exist.

At step 510, find the set of beamlets that are eligible for elimination, with thresholds in the conditions. Let E be the number of beamlets eligible for elimination.

At step 520, calculate b−E, where b denotes the number of beamlets. It is to be appreciated that in some cases an exact number of protobeams does not have to be achieved. Instead, if b−E is within a threshold amount from pb, then the method can proceed to step 560. These and other variations of the present principles are readily determined by one of ordinary skill in the art given the teachings of the present principles provided herein, while maintaining the spirit of the present principles.

At step 530, determine if (case 1) b−E>pb, (case 2) b−E<pb, or (case 3) b−E=pb. If (case 1), then proceed to step 540. If (case 2), then proceed to step 550. If (case 3), then proceed to step 560.

At step 540 (case 1, b−E>pb), determine if threshold adjustment options that increase the number of beamlets eligible for elimination have been exhausted. If so, then (unsuccessfully) terminate the method. Otherwise, then proceed to step 545. Note that limits may be placed on the condition-threshold values, e.g., to limit beamlet elimination to only beamlets that are completely dominated by another beamlet, the thresholds on the left-hand sides of both Condition 1 and Condition 2 can be set to 1, i.e., the thresholds are limited to being neither greater nor less than one. (This is what Option 2 (step 330B) does.) The limits can be upper bound or lower bounds or both. Meeting limits on the thresholds, for example, can constitute exhausting threshold adjustment options. Having already evaluated available adjustment options or reaching a loop counter maximum, e.g., on the number of times step 510 has been carried out, also can constitute exhausting threshold adjustment options.

At step 545, adjust thresholds to allow more beamlets to be eligible for elimination. Threshold adjustment to allow more beamlets to eligible for elimination can be done, for example, by decreasing the threshold on the left-hand side of Condition 1 in the algorithm or increasing the threshold on the left-hand side of Condition 2 or a combination of the two.

At step 550 (case 2, b−E<pb), choose whether or not to select a subset of the elimination-eligible beamlets to eliminate. The choice can depend, for example, on a trade-off between computation time (selection can be faster) versus solution quality. If selecting a subset, then go to step 553. Otherwise go to step 555.

At step 553, select, e.g., randomly, a subset of b−pb elimination-eligible beamlets to eliminate. The columns corresponding to the remaining beamlets are the protobeams, i.e., vpbmat is made up of the columns corresponding to the remaining beamlets. (The method would then proceed to step 340.)

At step 555, determine if threshold adjustment options that decrease the number of beamlets eligible for elimination have been exhausted. If so, then (unsuccessfully) terminate the method. If not, then proceed to step 557. As in step 540, limits can be set on condition-thresholds. Meeting limits on the thresholds, for example, can constitute exhausting threshold adjustment options. Having already evaluated available adjustment options or reaching a loop counter maximum, e.g., on the number of times step 510 has been carried out, also can constitute exhausting threshold adjustment options.

At step 557, adjust the thresholds to allow fewer beamlets to be eligible for elimination so that the lesser-dominated of the beamlets drop out of the set of elimination candidates. Threshold adjustment to allow fewer beamlets to eligible for elimination can be done, for example, by increasing the threshold on the left-hand side of Condition 1 in the algorithm or decreasing the threshold on the left-hand side of Condition 2 or a combination of the two.

At step 560 (case 3, b−E=pb), form vpbmat from the columns corresponding to the beamlets that are not in the set eligible for elimination.

Note that for Options 2 and 3, instead of finding the set of all beamlets eligible for elimination, it would be possible to evaluate beamlets for elimination one by one and terminate the process when only pb beamlets remain. The order of evaluation could then affect the set of beamlets determined to be eligible for elimination, so if quality is not sufficient in step 360, then in step 375, instead of adjusting pb or terminating the process unsuccessfully, the beamlets can be evaluated again in a different order. The same is true if a condition-threshold adjusting decision step replaces step 375, as described herein above.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method, comprising:
 condensing, by a processor, an original voxel-beamlet matrix stored in a memory device into a reduced dataset for proton beam simulation and therapy, the original voxel-beamlet matrix having a row for each of a plurality of voxels in a three-dimensional patient volume and a column for each of a plurality of radiation beamlets, wherein said condensing step comprises:
 determining protobeams to be extracted from the original voxel-beamlet matrix, the protobeams being columns (i) selected from the original voxel-beamlet matrix based on comparisons performed between the columns in the original voxel-beamlet matrix or (ii)

created by combining at least some of the columns in the original voxel-beamlet matrix, in a matrix condensing process;

extracting the protobeams from the original voxel-beamlet matrix; and storing the protobeams as the reduced dataset in the memory device.

2. The method of claim 1, wherein a target number of the protobeams to be extracted is at least one of user variable and user over-ridable.

3. The method of claim 1, wherein the protobeams to be extracted are determined by the hardware processor based on one or more metrics measuring at least one of a representation quality or a computation ease of the reduced dataset versus a target number of the protobeams to be extracted.

4. The method of claim 3, wherein the at least one of the representation quality and the computation ease is based on a stage of an overall treatment planning process being applied to a patient.

5. The method of claim 1, wherein the protobeams are selected from the original voxel-beamlet matrix based on the comparisons performed between the columns in the original voxel-beamlet matrix, subsequent to summing selected rows in any two of the columns being compared.

6. The method of claim 1, wherein the protobeams are extracted using a non-negative principal component analysis approach applied to the original voxel-beamlet matrix.

7. The method of claim 1, wherein the protobeams are selected from the original voxel-beamlet matrix further based on row labels in the original voxel-beamlet matrix.

8. The method of claim 7, wherein the row labels are assigned based on structure membership of a given row element to a given structure in a patient.

9. The method of claim 1, wherein the protobeams are selected from the original voxel-beamlet matrix irrespective of angle geometry information.

10. The method of claim 1, further comprising performing a radiation treatment plan using the reduced dataset.

11. The method of claim 1, further comprising performing, by a radiation therapy machine, a radiation therapy procedure on a patient using the reduced dataset.

12. The method of claim 1, wherein the protobeams are extracted as weighted combinations of the columns of the original voxel-beamlet matrix.

13. The method of claim 12, wherein respective weights of the weighted combinations of columns are determined based on a rotation matrix determined by performing a non-negative principle component analysis on the original voxel-beamlet matrix.

14. The method of claim 1, wherein the protobeams are selected based on domination amongst the protobeams implicated by the columns being compared.

15. The method of claim 14, wherein the domination is determined using one or more thresholds that relate to a particular structure in a patient.

16. A computer program product for extracting protobeams, the computer program product comprising a computer readable storage medium having program instructions embodied therewith, the program instructions executable by a computer to cause the computer to perform a method comprising:

condensing, by a processor, an original voxel-beamlet matrix stored in a memory device into a reduced dataset for proton beam simulation and therapy, the original voxel-beamlet matrix having a row for each of a plurality of voxels in a three-dimensional patient volume and a column for each of a plurality of radiation beamlets, wherein said condensing step comprises:

determining protobeams to be extracted from the original voxel-beamlet matrix, the protobeams being columns (i) selected from the original voxel-beamlet matrix based on comparisons performed between the columns in the original voxel-beamlet matrix or (ii) created by combining at least some of the columns in the original voxel-beamlet matrix, in a matrix condensing process;

extracting the protobeams from the original voxel-beamlet matrix; and storing the protobeams as the reduced dataset in the memory device.

17. The computer program product of claim 16, wherein the protobeams are extracted using a non-negative principal component analysis approach applied to the original voxel-beamlet matrix.

18. The computer program product of claim 16, wherein the protobeams are selected from the original voxel-beamlet matrix based on the comparisons performed between the columns in the original voxel-beamlet matrix, subsequent to summing selected rows in any two of the columns being compared.

19. The computer program product of claim 16, wherein the protobeams are selected based on domination amongst the protobeams implicated by the columns being compared.

20. A system, comprising:

a memory device configured to store an original voxel-beamlet matrix having a row for each of a plurality of voxels in a three-dimensional patient volume and a column for each of a plurality of radiation beamlets; and a hardware processor configured to condense the original voxel-beamlet matrix into a reduced dataset for proton beam simulation and therapy by determining protobeams to be extracted from the original voxel-beamlet matrix, and extracting the protobeams from the original voxel-beamlet matrix, the protobeams being columns (i) selected from the original voxel-beamlet matrix based on comparisons performed between the columns in the original voxel-beamlet matrix or (ii) created by combining at least some of the columns in the original voxel-beamlet matrix, in a matrix condensing process, wherein the protobeams are stored as the reduced dataset in the memory device.

* * * * *